United States Patent [19]

Buckman et al.

[11] 4,293,559

[45] Oct. 6, 1981

[54] SLIME CONTROL COMPOSITIONS AND METHODS OF USING THE SAME

[75] Inventors: John D. Buckman; Stanley J. Buckman; Betty S. Johnson; John D. Pera, all of Memphis, Tenn.

[73] Assignee: Buckman Laboratories, Inc., Memphis, Tenn.

[21] Appl. No.: 891,435

[22] Filed: Mar. 29, 1978

[51] Int. Cl.$^3$ ............................................. A01N 43/78
[52] U.S. Cl. ...................................... 424/270; 71/67; 162/161
[58] Field of Search .......................... 71/67; 424/270; 162/161

[56] References Cited

U.S. PATENT DOCUMENTS 3,520,976  6/1970  Buckman et al. .................. 424/270

*Primary Examiner*—Catherine L. Mills

*Attorney, Agent, or Firm*—Floyd Trimble

[57] ABSTRACT

The present invention relates to certain compositions and processes useful for inhibiting the growth of microorganisms in water and, in particular, water used for industrial purposes; for example, in the manufacture of paper, in cooling water systems in effluent water treatment, and in secondary recovery petroleum operations. The novel processes and compositions of the present invention are processes or mixtures which show unexpected synergistic activity against microorganisms, including bacteria, sulfate-reducing bacteria, fungi, and algae, which produce slime in aqueous systems where such slime is objectionable from either an operational or aesthetic point of view. Specifically, the invention is directed to the use of compositions comprising 2-(thiocyanomethylthio)benzothiazole and 2'-hydroxyethyl 2,3-dibromopropionate or 2'-hydroxyethyl 2-bromoacrylate.

8 Claims, No Drawings

SLIME CONTROL COMPOSITIONS AND METHODS OF USING THE SAME

BACKGROUND OF THE INVENTION

Many industrial products when wet or when subjected to treatment in water are normally susceptible to bacterial and/or fungal degradation or deterioration if means are not taken to inhibit such degradation or deterioration. Wood pulp, wood chips, starch and proteinaceous substances, animal hides, vegetable tanning liquors, and leather are all damaged or degraded by growth of bacteria and other microorganisms or by enzymes produced by such growth. Wet pulp containing above 25 percent moisture content is subject to attack by stain, mold, and decay fungi. If not controlled, the result is a loss of useful fiber in badly decayed pulp, difficulty in dispersing partially decayed pulp, a darkening in color, and the development of undesirable odors caused by the growth of the microorganisms. Different species of molds are encountered at various stages in the manufacture of leather. As an example, soaking provides an environment highly conducive to the growth of microorganisms, and even strong pickle solutions are subject to attack by some microorganisms. Mold in particular may be troublesome and cause discoloration of the pickled stock, especially if it is held for a period of time. During the chrome tanning process, the chrome tanned stock held "in the blue" readily molds and is discolored. Mold growth may develop on heavy vegetable tanned leather during the drying period and produce spots and stains on either the flesh or grain sides.

Another objectionable phenomenon occurring in industrial process systems involving water is slime formation. Slime consists of matted deposits of microorganisms, fibers, and debris, and it may be stringy, pasty, rubbery, tapioca-like, hard, or horny, and it may have a characteristic odor that is different from that of the liquid suspensions in which it is formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeasts, and yeast-like organisms.

Besides being objectionable from the standpoint of general cleanliness and sanitation in breweries, wineries, dairies, paper mills, and other industrial plants or establishments, slime may interfere and produce plugging of screens in pulp and paper systems, thus reducing their efficiency. When large amounts of slime become incorporated in the paper sheet, its strength is reduced, and it may consequently break and require rethreading of the machine. In the paper itself, slime may be responsible for unsightly spots, holes, and odors and may produce general discoloration throughout the sheet.

Sulfate-reducing bacteria are generally present in waters used for the secondary recovery of petroleum. The presence of these bacteria is objectionable if not controlled. For example, these organisms are able to reduce sulfates present in the injection water to sulfides which in turn react with soluble iron salts to form insoluble iron sulfide. As a result, matted deposits are produced consisting of sulfides, occluded oil, plus any other solids that may be present. This is undesirable because water containing such deposits when injected into subterranean formations causes the plugging thereof. Furthermore, sulfate-reducing bacteria cause corrosion of metal by accelerating galvanic action. Microbiological corrosion is well recognized and is a major economic problem in the petroleum industry.

It is, therefore, a principal object of the present invention to provide a composition for the control of microorganisms that are responsible for the formation of slime in aqueous systems.

It is another object of this invention to provide an improved process for controlling slime-forming microorganisms in aqueous systems such as pulp and paper mill systems, cooling water systems, and secondary recovery petroleum operations.

These and other objects and advantages of the novel compositions and processes of this invention will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

In brief, the foregoing objects and advantages are obtained by utilizing compositions comprising synergistic mixtures of 2-(thiocyanomethylthio)benzothiazole and one of the esters selected from 2'-hydroxyethyl 2,3-dibromopropionate and 2'-hydroxyethyl 2-bromoacrylate.

The compositions of this invention are utilized for controlling the growth and reproduction of slime-forming microorganisms by adding the compositions to cooling water systems, pulp and paper mill systems, pools, ponds, lagoons, lakes, etc., in an amount sufficient to control the slime-forming microorganisms which are present in the system which is treated.

The organic microbicides comprising the compositions of this invention are commercially available compounds or easily synthesized from commercially available raw materials. The preparation of 2-(thiocyanomethylthio)benzothiazole is described in U.S. Pat. No. 3,520,976. The addition of bromine to 2'-hydroxyethyl acrylate produces 2'-hydroxyethyl 2,3-dibromopropionate in good yield. This latter compound may then be dehydrobrominated with an alkaline reagent to prepare 2'-hydroxyethyl 2-bromoacrylate in good yield. Alkaline reagents suitable for the dehydrobromination reaction include aliphatic and heterocyclic tertiary amines, ammonia, sodium hydroxide, and sodium carbonate.

The ratios of the 2-(thiocyanomethylthio)benzothiazole to the brominated ester in the compositions of this invention are adjusted to provide a synergistic behavior to the composition. These synergistic weight ratios range from about 95:5 parts of 2-(thiocyanomethylthio)-benzothiazole to 5:95 parts of the brominated ester selected from 2'-hydroxyethyl 2,3-dibromopropionate and 2'-hydroxyethyl 2-bromoacrylate. When the microbicides are present in these ratios, the resulting composition possesses a higher degree of effectiveness against slime-forming microorganisms than the individual microbicides comprising the mixture.

As to the amount of the compositions to be added to the various systems, suitable and preferred quantities vary according to the specific system in which the compositions are used. When added to aqueous systems to control slime-forming microorganisms, the suitable and preferred quantities vary from 0.1 to 1000 parts and 0.1 to 100 parts, respectively, per million parts of water present in the system. It will be understood, of course, that larger quantities of the compositions may be used with no detrimental effect, but such larger quantities increase the cost of treatment with limited material benefit.

In order to disclose the nature of the invention still more clearly, the following illustrative examples will be given. It is understood, however, that the invention is not to be limited to the specific conditions or details set forth in these examples, except insofar as such limitations are specified in the appended claims.

EXAMPLE 1

The compound 2'-hydroxyethyl 2,3-dibromopropionate is easily dehydrobrominated under even slightly alkaline conditions to 2'-hydroxyethyl 2-bromoacrylate. To demonstrate the speed of this reaction under mild conditions, a one percent suspension of 2'-hydroxyethyl 2,3-dibromopropionate in water buffered to pH 7.5 was shaken for 20 hours at 25° C. The ionic bromide was determined by titration with standard silver nitrate solution and this analysis indicated that 90.5 percent of the dibromopropionate had been converted to the 2'-hydroxyethyl 2-bromoacrylate.

In order to prepare larger quantities of the 2'-hydroxyethyl 2-bromoacrylate, 202.2 grams (2.0 moles) of triethylamine was added to a solution of 551.7 grams (2.0 moles) of 2'-hydroxyethyl 2,3-dibromopropionate in 670 grams of methylene chloride, containing 0.6 gram of methylhydroquinone, over a two-hour period. The reaction mixture was agitated for 16 hours, and the precipitated triethylamine hydrobromide was removed by filtration. The filtrate was then washed with two 250-milliliter portions of water. After drying, the solution was distilled to remove the methylene chloride under reduced pressure. The yield of 2'-hydroxyethyl 2-bromoacrylate was 337.7 grams (86 percent).

EXAMPLE 2

In this example, synergism was demonstrated in separate experiments by testing 2-(thiocyanomethylthio)-benzothiazole, designated as Compound B, and 2'-hydroxyethyl 2,3-dibromopropionate, designated as Compound A, in one series of tests in varying ratios and over a range of concentrations against *Aspergillus niger*. In the second series of tests, Compound B was compared with 2'-hydroxyethyl 2-bromoacrylate, designated as Compound C. The compounds and mixtures were tested by the pulp-substrate method described in U.S. Pat. No. 3,193,448, which disclosure is hereby made a part of this application. The lowest concentration of each compound or mixture which completely prevented growth of the fungi was taken as the end point. End points for the various mixtures were then compared with end points for the pure active ingredients alone in concomitantly prepared flasks. Synergism was demonstrated by the method described by Kull, F. C., Eisman, P. C., Sylwestrowicz, H. D., and Mayer, R. L., Applied Microbiology 9, 538–541 (1961) wherein $$\frac{Q_A}{Q_a} + \frac{Q_B}{Q_b} \text{ is less than 1}$$

$Q_A$ = Concentration of Compound A in parts per million, acting alone, which produced an end point.
$Q_B$ = Concentration of Compound B, in parts per million, acting alone, which produced an end point.
$Q_a$ = Concentration of Compound A, in parts per million, in the mixture, which produced an end point.
$Q_b$ = Concentration of Compound B, in parts per million, in the mixture, which produced an end point.

When Compound C was being tested, $Q_A$ and $Q_a$ would become $Q_C$ and $Q_c$.

When the sum of $Q_A/Q_a$ and $Q_B/Q_b$ is greater than one, antagonism is indicated and when the sum is equal to one, additivity is indicated. When the sum of this value is less than 1, synergism exists.

This procedure for demonstrating the synergism of the compositions of this invention is a widely used and acceptable procedure. More detailed information is provided in the article by Kull et al. Further information concerning this procedure is contained in U.S. Pat. No. 3,231,509, which disclosure is hereby made a part of this application.

The results obtained in this Example are included in Table 1.

TABLE 1

Test organism: *Aspergillus niger*

Experiment 1
Quantities producing end points

| Weight ratio of A to B | $Q_A$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
| --- | --- | --- | --- | --- | --- | --- |
| | Parts per million | | | | | |
| 100/0 | 12 | — | 12 | — | — | — |
| 87/13 | 4.4 | 0.6 | 5 | 0.37 | 0.12 | 0.49 |
| 80/20 | 5.6 | 1.4 | 7 | 0.47 | 0.28 | 0.75 |
| 73/27 | 3.7 | 1.3 | 5 | 0.31 | 0.26 | 0.57 |
| 67/33 | 3.3 | 1.7 | 5 | 0.28 | 0.34 | 0.62 |
| 0/100 | — | 5 | 5 | — | — | — |

Experiment 2
Quantities producing end points

| Weight ratio of B to C | $Q_B$ | $Q_C$ | Mixture | $\frac{Q_B}{Q_b}$ | $\frac{Q_C}{Q_c}$ | $\frac{Q_B}{Q_b} + \frac{Q_C}{Q_c}$ |
| --- | --- | --- | --- | --- | --- | --- |
| | Parts per million | | | | | |
| 0/100 | — | 6 | 6 | — | — | — |
| 5/95 | 0.2 | 3.8 | 4 | 0.1 | 0.63 | 0.73 |
| 95/5 | 1.9 | 0.1 | 2 | 0.95 | 0.02 | 0.97 |
| 100/0 | 2.0 | — | 2 | — | — | — |

EXAMPLE 3

The effectiveness of Compounds A, B, and C described in Example 2 and of mixtures of A and B as well as B and C was determined against *Enterobacter aerogenes* at pH 5.5 using the pulp-substrate method described in U.S. Pat. No. 2,881,070, which disclosure is hereby made a part of this application. The method described in Example 2 was then used to demonstrate that a synergistic effect was also obtained in controlling the test bacterium. The end point in these calculations was the concentration in parts per million required for 80 percent kill. The results of these tests are described in Table 2.

TABLE 2

Test organism: *Enterobacter aerogenes*

Experiment 1
Quantities producing end points

| Weight ratio of A to B | $Q_A$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
| --- | --- | --- | --- | --- | --- | --- |
| | Parts per million | | | | | |
| 100/0 | 15 | — | 15 | — | — | — |
| 80/20 | 12 | 3 | 15 | 0.80 | 0.05 | 0.85 |
| 67/33 | 10.05 | 4.95 | 15 | 0.67 | 0.09 | 0.76 |

TABLE 2-continued

| | | | Experiment 2 Quantities producing end points | | | |
|---|---|---|---|---|---|---|
| 0/100 | — | 55 | 55 | — | — | — |

| Weight ratio of B to C | $Q_B$ | $Q_C$ Parts per million | Mixture | $\frac{Q_B}{Q_b}$ | $\frac{Q_C}{Q_c}$ | $\frac{Q_B}{Q_b} + \frac{Q_C}{Q_c}$ |
|---|---|---|---|---|---|---|
| 0/100 | — | 4 | — | — | — | — |
| 5/95 | 0.2 | 3.8 | 4 | 0.004 | 0.95 | 0.954 |
| 50/50 | 2.0 | 2.0 | 4 | 0.04 | 0.5 | 0.54 |
| 95/5 | 9.5 | 0.5 | 10 | 0.19 | 0.12 | 0.31 |
| 100/0 | 50 | — | — | — | — | — |

EXAMPLE 4

The effectiveness of Compounds A, B, and C described in Example 2 and of mixtures of A and B as well as B and C was determined against the three algae *Chlorella pyrenoidosa*, *Chlorococcum hypnosporum*, and *Phormidium inundatum* in Difco algae broth having the following composition:

| Compound | Ingredients per liter |
|---|---|
| Sodium nitrate | 1.0 gram |
| Ammonium chloride | 50.0 milligrams |
| Calcium chloride | 58.0 milligrams |
| Magnesium sulfate | 0.513 gram |
| Dipotassium phosphate | 0.25 gram |
| Ferric chloride | 3.0 grams |

Forty-gram portions of the algae medium were added to 250-milliliter Pyrex Erlenmeyer flasks fitted with loose metal caps and then sterilized. Each of the following substances were then added to the flasks in the order listed:
1. Sterile algae medium as required in each individual case to bring the total weight of the contents of each flask to 50 grams, after allowing for all subsequent additions specified hereinafter.
2. Solution of toxicant or control agent to be evaluated in each test to give the concentration desired in parts per million by weight.
3. *Chlorella pyrenoidosa*, *Chlorococcum hypnosporum*, and *Phormidium inundatum* are the algae used for these tests. The inoculum was an amount sufficient to give excellent growth in the controls after 14 days. This was achieved by adding one milliliter of a 14-day-old culture having luxuriant growth.

The *Chlorella pyrenoidosa* culture was obtained from The American Type Culture Collection No. 7516; *Chlorococcum hypnosporum*, Starr No. 119, was obtained from the Culture Collection of Algae at Indiana University, Bloomington, Ind.; *Phormidium inundatum* was obtained from the University of Wisconsin, Madison, Wis.

After the inoculum of the test algae had been added, the flasks were allowed to incubate at a temperature of 28°±2° C. under fluorescent illumination of 250 footcandle intensity (8 hours, 16 hours darkness) for a period adequate for growth in the controls (those portions of medium which contained no toxicant). Observations of growth were made after 28 days on the basis of the following key:
 4=Excellent
 3=Good
 2=Poor
 1=Very poor, scant, questionable
 0=No growth The results are summarized in Table 3. Synergism is apparent when *Phormidium inundatum* was the test organism.

TABLE 3

Inhibition of *Chlorella pyrenoidosa*, *Chlorococcum hypnosporum*, and *Phormidium inundatum* in Difco Algae Broth after 28 days' incubation

| Test organism | Concentration Parts per million | A | 80A/ 20B | 67A/ 33B | B | 95B/ 5C | 50B/ 50C | 5B/ 95C | C |
|---|---|---|---|---|---|---|---|---|---|
| | | | | | Growth | | | | |
| Chlorella pyrenoidosa | 0.5 | 4 | 4 | 4 | 4 | 4 | 4 | 4 | 4 |
| | 1 | 4 | 4 | 4 | 0 | 0 | 0 | 3 | 4 |
| | 2 | 4 | 0 | 4 | 0 | 0 | 0 | 0 | 2 |
| | 4 | 0 | 0 | 0 | 0 | 0 | 0 | 0 | 0 |
| | 8 | 0 | 0 | 0 | 0 | 0 | 0 | 0 | 0 |
| Chlorococcum hypnosporum | 0.5 | 4 | 4 | 4 | 0 | 0 | 3 | 4 | 4 |
| | 1 | 4 | 4 | 3 | 0 | 0 | 0 | 4 | 4 |
| | 2 | 4 | 0 | 0 | 0 | 0 | 0 | 3 | 4 |
| | 4 | 3 | 0 | 0 | 0 | 0 | 0 | 0 | 0 |
| | 8 | 0 | 0 | 0 | 0 | 0 | 0 | 0 | 0 |
| Phormidium unundatum | 0.5 | 4 | 4 | 4 | 4 | 4 | 4 | 4 | 4 |
| | 1 | 4 | 4 | 4 | 4 | 4 | 4 | 4 | 4 |
| | 2 | 4 | 2 | 3 | 2 | 0 | 0 | 4 | 4 |
| | 4 | 1 | 0 | 0 | 0 | 0 | 0 | 0 | 0 |
| | 8 | 0 | 0 | 0 | 0 | 0 | 0 | 0 | 0 |

EXAMPLE 5

In this example, the effect of a composition comprising 25 parts of 2'-hydroxyethyl 2,3-dibromopropionate and five parts by weight of 2-(thiocyanomethylthio)-benzothiazole on the growth of the sulfate-reducing bacterium *Desulfovibrio desulfuricans* was determined using the method described in Example 11 of U.S. Pat. No. 3,520,976, which disclosure is hereby made of this application. The growth of the organism was completely inhibited by 4.5 to 7.5 parts per million of the composition tested.

Among the microorganisms that are responsible for the growth of slime in pulp and paper mills are the bacterium *Enterobacter aerogenes* and the fungi *Aspergillus niger*, *Penicillium roqueforti*, and *Chaetomium globosum*. Algae are not ordinarily considered as major slime-forming organisms in pulp and paper mills, but algae do develop in the fresh water supplies in some instances. In cooling towers, algae are a major cause of fouling and reduced efficiency in addition to bacteria and fungi. The sulfate-reducing bacteria that is most often responsible for problems in secondary recovery petroleum operations and other aqueous systems is *Desulfovibrio desulfuricans*. It is, thus, apparent from the experimental data described in the foregoing Examples that the compositions of this invention will provide control of slime-forming microorganisms in aqueous systems.

The compositions of this invention may be used diluted with a carrier which may be liquid or solid. Dusts may be prepared with a finely divided solid such as talc, clay, pyrophyllite, diatomaceous earth, hydrated silica, calcium silicate, or magnesium carbonate. If desired, wetting and/or dispersing agents may be used. When the proportions of these are increased, there results a wettable powder, which may be dispersed in water and applied from a spray.

Dusts may contain one percent to 15 percent of the compounds of this invention, while wettable powders may contain up to 50 percent or more of one or more of these compounds.

A typical formulation of a wettable powder comprises 20 percent to 50 percent of the compositions of this invention, 45 percent to 75 percent of one or more finely divided solids, one percent to five percent of a wetting agent, and one percent to five percent of a dispersing agent. Typical wetting agents include sodium dodecyl sulfate, sodium nonylbenzene sulfonate, sodium dioctyl sulfosuccinate, octylphenoxypolyethoxyethanol, or other nonionic agents, such as ethylene and/or propylene oxide condensates with long chained alcohols, mercaptans, amines, or carboxylic acids. Typical dispersing agents include the sodium sulfonate of condensed naphthalene-formaldehyde and lignin sulfonates.

Liquid concentrates may also be used. These are prepared by taking up the compositions of this invention in an organic solvent together with one or more surface active agents.

The compounds of this invention may be used in conjunction with other microbicidal agents and also in conjunction with miticides or insecticides or other pesticides.

While particular embodiments of the invention have been described, it will be understood, of course, that the invention is not limited thereto since many modifications may be made, and it is, therefore, contemplated to cover by the appended claims any such modifications as fall within the true spirit and scope of the invention.

The invention having thus been described, what is claimed and desired to be secured by Letters Patent is:

1. A bactericidal and fungicidal synergistic composition consisting essentially of about 15 to about 85 parts by weight of 2-(thiocyanomethylthio)benzothiazole and about 85 to about 15 parts by weight of a compound selected from 2'-hydroxyethyl 2,3-dibromopropionate and 2'-hydroxyethyl 2-bromoacrylate.

2. A bactericidal and fungicidal synergistic composition consisting essentially of about 15 to about 85 parts by weight of 2-(thiocyanomethylthio)benzothiazole and about 85 to about 15 parts by weight of 2'-hydroxyethyl 2,3-dibromopropionate.

3. A bactericidal and fungicidal synergistic composition consisting essentially of about 15 to about 85 parts by weight of 2-(thiocyanomethylthio)benzothiazole and about 85 to about 15 parts by weight of 2'-hydroxyethyl 2-bromoacrylate.

4. A bactericidal and fungicidal synergistic composition consisting essentially of 20 to 30 parts by weight of 2-(thiocyanomethylthio)benzothiazole and 5 to 10 parts by weight of 2'-hydroxyethyl 2,3-dibromopropionate.

5. The method of controlling the growth and deposition of slime-forming organisms in flowing-water systems which comprises adding to the flowing water in such system a composition as defined in claim 1 in an amount between approximately 0.1 and approximately 100 parts per million of the water.

6. The method of controlling the growth and proliferation of sulfate-reducing bacteria as well as species of slime-forming microorganisms in secondary recovery petroleum operations, which comprises adding to the water in such systems a composition as defined in claim 1 in an amount between approximately 0.1 and approximately 100 parts per million of the water.

7. The method of controlling the growth and proliferation of bacteria and fungi in fresh water which comprises adding to said fresh water the composition defined in claim 1 in an amount between approximately 0.1 and approximately 100 parts per million of the water.

8. The method of controlling the growth and proliferation of bacteria and fungi in cooling water which comprises adding to said cooling water the composition defined in claim 1 in an amount between approximately 0.1 and approximately 100 parts per million of the water.

* * * * *